United States Patent [19]

Virtanen et al.

[11] Patent Number: 4,670,455

[45] Date of Patent: Jun. 2, 1987

[54] METHOD OF BRINGING ABOUT SEDATION AND/OR ANALGESIA IN A MAMMAL

[75] Inventors: Raimo E. Virtanen, Rusko; Arto J. Karjalainen; Kauko O. A. Kurkela, both of Oulu; Antti T. Vaha-Vahe; Outi M. Vainio-Kivinen, both of Turku, all of Finland

[73] Assignee: Farmos-Yhtyma Oy, Turku, Japan

[21] Appl. No.: 804,197

[22] Filed: Dec. 3, 1985

[30] Foreign Application Priority Data

Dec. 4, 1984 [FI] Finland ................................. 844786

[51] Int. Cl.$^4$ ........................................... A61K 31/415
[52] U.S. Cl. .................................................. 514/396
[58] Field of Search ......................................... 514/396

[56] References Cited

U.S. PATENT DOCUMENTS 4,544,664 10/1985 Karjalainen ......................... 514/396

OTHER PUBLICATIONS

Chem. Abst. 99-38462j (1983).
O. Vainio: "Detomidine HCl-A Novel Imidazole Type Sedative Analgesic, Pharmacologie et Toxicologie Veterinaires, Inra Publ. Paris, 1982, Les Colloques de l'INRA, No. 8.

Primary Examiner—Stanley J. Friedman
Attorney, Agent, or Firm—Armstrong, Nikaido, Marmelstein & Kubovcik

[57] ABSTRACT

4-[(α-Methyl)-2,3-dimethyl-benzyl]imidazole is useful as a veterinary sedative-analgetic agent, especially in small mammals.

2 Claims, No Drawings

METHOD OF BRINGING ABOUT SEDATION AND/OR ANALGESIA IN A MAMMAL

This invention relates to sedative and analgesic agents useful in the veterinary field.

4-[(α-Methyl)-2,3-dimethyl-benzyl]imidazole of the formula

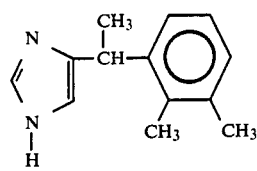

(I)

has been disclosed in the European Patent Publication No. 72615 as an antihypertensive agent. 4-(2,3-Dimethylbenzyl)-imidazole, or detomidine, is a known sedative and analgesic agent useful in horses and cattle. Detomidine is used in veterinary medicine as a pharmacological restraint to keep the animal sedated before investigation, treatment and difficult medical operations. Even a small surgical operation cannot be carried out without the use of a sedative agent. The effect of detomidine in horses and cattle has been described in the literature, e.g. O. Vainio: "Detomidine hydrochloride—a noval imidazole-type sedative-analgesic". Pharmacologie et Toxicologie Veterinaires, INRA Publ. Paris, 1982, Les Colloques de l'INRA, No. 8. There is also a great need for sedative-analgesic agents as pharmacological restraints in the treatment of dogs, cats and other small animals, but no useful effect was, however, observed.

We have now surprisingly found that the above-mentioned detomidine analogue, 4-[(α-methyl)-2,3-dimethylbenzyl]imidazole (compound (I)) is very effective as a sedative-analgesic in the treatment of small animals, especially dogs and cats, but also, e.g., guinea pigs and rabbits. Intramuscular or intravenous administration of this compound at a dose of 10 to 160 μg/kg (in dogs and cats) or 200 to 400 μg/kg (in guinea pigs and rabbits) induces a sedative effect which appears in 2 to 10 minutes after intramuscular (i.m.) administration or in 0.5 to 1 min. after intravenous (i.v.) administration. Both the strength and the duration of the effects are clearly dose dependant. Higher doses have a hypnotic effect during which the animals do not react to external stimuli such as sounds, pain etc. The duration of the effect is about 1 to 4 hours in dogs and 0.5 to 2 hours in cats. Sedation is accompanied by an analgesic effect, especially at higher doses. This compound possesses both a sedative and an analgesic effect, which are clearly superior to those of xylazine, which is a known compound commonly used as sedative in the treatment of small animals. The following test data illustrate the invention. The tests were carried out using six beagle dogs per group. The study was carried out using a cross-over-design. Different doses of compound (I) were given i.m. or i.v.. The reactions observed were compared to those obtained by xylazine.

TABLE 1

| | Reaction to sounds | | | | | | | | | |
|---|---|---|---|---|---|---|---|---|---|---|
| | compound (I) | | | | | | xylazine | | | |
| dose, μg/kg | 40 | | 80 | | 60 | | 1500 | | 3000 | |
| administration | i.m. | i.v. | i.m. | i.v. | i.m. | i.v. | i.m. | i.v. | i.m. | i.v. |
| results (number of dogs): | | | | | | | | | | |
| normal reaction | — | 1 | — | — | — | — | 6 | 4 | 2 | 2 |
| weak reaction | 3 | — | — | — | 1 | 1 | — | 2 | 3 | 4 |
| no reaction | 3 | 5 | 6 | 6 | 5 | 5 | — | — | 1 | — |
| total number of dogs | 6 | 6 | 6 | 6 | 6 | 6 | 6 | 6 | 6 | 6 |

TABLE 2

| | Duration of the sedation | | | | | | | | | |
|---|---|---|---|---|---|---|---|---|---|---|
| | compound (I) | | | | | | xylazine | | | |
| dose, μg/kg | 40 | | 80 | | 160 | | 1500 | | 3000 | |
| administration | i.m. | i.v. | i.m. | i.v. | i.m. | i.v. | i.m. | i.v. | i.m. | i.v. |
| duration: | | | | | | | | | | |
| 0–15 min | — | — | — | — | — | — | 4 | 2 | 2 | 1 |
| 15–30 min | 2 | 2 | — | — | — | — | 2 | 4 | 3 | 4 |
| 30–60 min | 4 | 4 | 3 | 4 | 1 | 2 | — | — | 1 | 1 |
| 1–2 h | — | — | 3 | 2 | 3 | 3 | — | — | — | — |
| >2 h | — | — | — | — | 2 | 1 | — | — | — | — |
| total number of dogs | 6 | 6 | 6 | 6 | 6 | 6 | 6 | 6 | 6 | 6 |

TABLE 3

| | First signs of sedation | | | |
|---|---|---|---|---|
| | mean, min | | variation, min | |
| | i.m. | i.v. | i.m. | i.v. |
| compound (I), 40 μg/kg | 5 | 0.7 | 3–10 | 0.5–1 |
| compound (I), 80 μg/kg | 3 | 0.6 | 2–6 | 0.5–1 |
| compound (I), 160 μg/kg | 2 | 0.5 | 2–3 | 0.5–0.5 |
| xylazine, 1500 μg/kg | 4 | 2 | 2–8 | 0.5–10 |
| xylazine, 3000 μg/kg | 2 | 0.5 | 2–3 | 0.5–0.5 |

TABLE 4

| | Evaluation of the sedative effect | | | | | | | | | |
|---|---|---|---|---|---|---|---|---|---|---|
| | compound (I) | | | | | | xylazine | | | |
| dosage, μg/kg | 40 | | 80 | | 160 | | 1500 | | 3000 | |
| administration | i.m. | i.v. | i.m. | i.v. | i.m. | i.v. | i.m. | i.v. | i.m. | i.v. |
| no activity | — | — | — | — | — | — | — | — | — | — |
| some activity | — | 1 | — | — | — | — | 6 | 6 | 2 | 3 |
| good activity | 6 | 5 | 6 | 6 | 6 | 6 | — | — | 4 | 3 |
| total no of dogs | 6 | 6 | 6 | 6 | 6 | 6 | 6 | 6 | 6 | 6 |

TABLE 5

| | Evaluation of the analgesic effect | | | | | | | | | |
|---|---|---|---|---|---|---|---|---|---|---|
| | compound (I) | | | | | | xylazine | | | |
| dosage, μg/kg | 40 | | 80 | | 160 | | 1500 | | 3000 | |
| administration | i.m. | i.v. | i.m. | i.v. | i.m. | i.v. | i.m. | i.v. | i.m. | i.v. |
| no activity | — | — | — | — | — | — | — | — | — | — |
| some activity | 1 | 3 | — | — | — | — | 6 | 6 | 4 | 5 |
| good activity | 5 | 3 | 6 | 6 | 6 | 6 | — | — | 2 | 1 |
| total no of dogs | 6 | 6 | 6 | 6 | 6 | 6 | 6 | 6 | 6 | 6 |

TABLE 6

| | The position of the animal during the maximum effect | | | | | | | | | |
|---|---|---|---|---|---|---|---|---|---|---|
| | compound (I) | | | | | | xylazine | | | |
| dosage, μg/kg | 40 | | 80 | | 160 | | 1500 | | 3000 | |
| administration | i.m. | i.v. | i.m. | i.v. | i.m. | i.v. | i.m. | i.v. | i.m. | i.v. |
| position: | | | | | | | | | | |
| standing | — | — | — | — | — | — | 1 | — | — | — |
| able to get up easily | — | — | — | — | — | — | 4 | 4 | 2 | 2 |
| able to get up with difficulty | 3 | 3 | 1 | — | — | 1 | 1 | 2 | 4 | 4 |
| not able to get up | 3 | 3 | 5 | 6 | 6 | 5 | — | — | — | — |
| total no of dogs | 6 | 6 | 6 | 6 | 6 | 6 | 6 | 6 | 6 | 6 |

We claim:

1. A method of bringing about sedation and/or analgesia in a small mammal which comprises administering by injection to a small mammal requiring such treatment an effective amount of 4-[(α-methyl)-2,3-dinethylbenzyl]imidazole.

2. A method according to claim 1 in which a sedative effect is produced in a dog or cat by administration by injection of a dosage of 10 to 100 μg/kg.

* * * * *

UNITED STATES PATENT AND TRADEMARK OFFICE
CERTIFICATE OF CORRECTION

PATENT NO.    : 4,670,455

DATED         : June 2, 1987

INVENTOR(S)   : Virtanen et al.

It is certified that error appears in the above-indentified patent and that said Letters Patent is hereby corrected as shown below:

In the Claim

Column 4, line 40 (claim 1, line 4), delete "dinethyl" and substitute therefor --dimethyl--.

Signed and Sealed this

Twenty-second Day of July, 1997

Attest:

BRUCE LEHMAN

Attesting Officer

Commissioner of Patents and Trademarks